United States Patent [19]

Harris et al.

[11] 4,383,125
[45] May 10, 1983

[54] ALDEHYDE-ETHERS

[75] Inventors: Norman Harris, Stockton-on-Tees; Alan J. Dennis, Middlesbrough; George E. Harrison, Billericay, all of England

[73] Assignee: Davy McKee (Oil & Chemicals) Limited, London, England

[21] Appl. No.: 139,591

[22] Filed: Apr. 11, 1980

[30] Foreign Application Priority Data

Apr. 11, 1979 [GB] United Kingdom ............... 7912849

[51] Int. Cl.$^3$ .......................................... C07C 47/198
[52] U.S. Cl. .................................. 568/496; 568/454; 568/497; 568/671
[58] Field of Search ............... 568/454, 448, 496, 497, 568/671, 672

[56] References Cited

U.S. PATENT DOCUMENTS

| | | | |
|---|---|---|---|
| 2,170,854 | 8/1939 | Drake | 568/496 |
| 2,555,950 | 6/1942 | Wilson | 568/496 |
| 3,518,310 | 6/1970 | Lutz | 568/496 |
| 3,527,809 | 9/1970 | Pruett | 568/454 |
| 3,676,500 | 7/1972 | Mantell et al. | 568/496 |
| 3,764,712 | 10/1972 | Kulka | 568/496 |
| 4,029,710 | 6/1977 | Suzuki | 568/768 |

FOREIGN PATENT DOCUMENTS 1338237 11/1973 United Kingdom ............... 568/454

OTHER PUBLICATIONS

Adkins et al., "J. Amer. Chem. Soc.", vol. 71, p. 3051, (1949).
Hill et al., "J. Amer. Chem. Soc.", vol. 77, pp. 3889–3892, (1955).

Primary Examiner—Werren B. Lone

Attorney, Agent, or Firm—Bernard, Rothwell & Brown

[57] ABSTRACT

Aldehyde ethers of the general formula

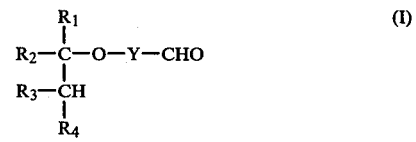

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, and wherein Y represents $-CH_2-CH_2-C_2$ or $-CH_2-CH(CH_3)-$, are prepared by hydroformylation of a corresponding compound of formula:

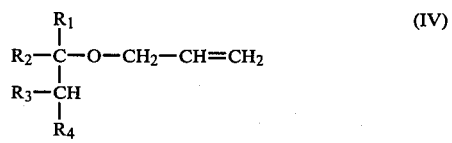

by reaction with hydrogen and carbon monoxide in the presence of a hydroformylation catalyst, e.g. a rhodium complex catalyst. Preferred compounds include 4-t-butoxybutyraldehyde and 3-t-butoxy-2-methylpropionaldehyde. The compounds are useful chemical intermediates in the production of, for example, butane-1,4-diol, butyrolactone and tetrahydrofuran.

5 Claims, No Drawings

ALDEHYDE-ETHERS

This invention relates to novel aliphatic aldehyde-ethers and to their preparation.

According to the invention there are provided novel aliphatic aldehyde-ethers of the general formula:

$$R_2-\underset{\underset{R_4}{\overset{\overset{R_1}{|}}{R_3-CH}}}{\overset{|}{C}}-O-Y-CHO \qquad (I)$$

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, and wherein Y represents $-CH_2-CH_2-CH_2-$ or $-CH_2-CH(CH_3)-$.

Preferably $R_1$ and $R_2$ each represent, independently of the other, a methyl or ethyl group, $R_3$ represents a hydrogen atom or a methyl group and $R_4$ represents a hydrogen atom. Particularly preferred compounds of formula (I) are:

$$(CH_3)_3C-O-CH_2-CH_2-CH_2-CHO \qquad (II)$$

and $$(CH_3)_3C-O-CH_2-CH(CH_3)-CHO \qquad (III)$$

The invention further provides a process for the preparation of a compound of formula (I) which comprises contacting a compound of the general formula:

$$R_2-\underset{\underset{R_4}{\overset{\overset{R_1}{|}}{R_3-CH}}}{\overset{|}{C}}-O-CH_2-CH=CH_2 \qquad (IV)$$

wherein $R_1$, $R_2$, $R_3$ and $R_4$ are as defined above, with hydrogen and carbon monoxide under hydroformylation conditions and in the presence of a catalytic amount of a hydroformylation catalyst.

The formation of compounds of formula (I) can be represented by the following equation:

$$R_2-\underset{\underset{R_4}{\overset{\overset{R_1}{|}}{R_3-CH}}}{\overset{|}{C}}-O-CH_2-CH=CH_2 \xrightarrow[\text{Catalyst}]{H_2 + CO} \qquad (IV)$$

$$R_2-\underset{\underset{R_4}{\overset{\overset{R_1}{|}}{R_3-CH}}}{\overset{|}{C}}-O-CH_2-CH_2-CH_2-CHO \,+ \qquad (V)$$

$$R_2-\underset{\underset{R_4}{\overset{\overset{R_1}{|}}{R_3-CH}}}{\overset{|}{C}}-O-CH_2-CH(CH_3)-CHO \qquad (VI)$$

The invention also extends to the compounds of formulae (V) and (VI) per se.

Depending on the choice of catalyst and on the hydroformylation conditions used, the proportions of the compounds of formulae (V) and (VI) formed may vary.

The hydroformylation catalyst may be any Group VIII metal-containing hydroformylation catalyst known to be effective for catalysing the hydroformylation of terminal olefins. Typical of such catalysts are those containing, for example, cobalt, iridium, ruthenium, platinum and rhenium. Preferably, however, the catalyst is a rhodium-containing catalyst.

The hydroformylation conditions used will depend on the catalyst chosen. When using a cobalt-containing catalyst, such as a dicobalt octacarbonyl $Co_2(CO)_8$, suitable reaction conditions may include use of an inert solvent, such as benzene, an operating temperature of, for example 120°–125° C., a partial pressure of hydrogen of about 100 to about 150 kg/cm² absolute, and a partial pressure of carbon monoxide of about 100 to about 150 kg/cm² absolute. The use of such conditions for the hydroformylation of allyl ethyl ether has been described (see H. Adkins and G. Krsek, J. Amer Chem. Soc., 71, 3051 (1949)). These authors reported that allyl ethyl ether under these conditions yielded 30% β-ethoxyisobutyraldehyde, 6% methylacrolein and 4% γ-ethoxybutyraldehyde.

When a rhodium-containing catalyst is used, the reaction can be carried out at lower pressures, for example about 30 kg/cm² absolute or less, typically at about 20 kg/cm² absolute or less. Moreover since rhodium-containing hydroformylation catalysts are generally involatile, it is usually much easier to recover the reaction products than when using cobalt catalysts, which tend to be volatile. The aldehyde-ethers of formula (I) are generally relatively volatile and can be recovered overhead from the reaction mixture.

In a particularly preferred process the hydroformylation catalyst is a rhodium complex catalyst comprising rhodium in complex combination with carbon monoxide and a triorganophosphine ligand, such as triphenylphosphine. This catalyst is preferably free from halogen, such as chlorine. Usually the catalyst will be present in solution.

The concentration of rhodium in the reaction medium can range from about 5 parts per million by weight up to about 1000 parts per million of rhodium or more, calculated as rhodium metal. However, because rhodium is a scarce and valuable metal it will usually be preferred to operate at the lowest rhodium concentration that is consistent with achieving a practicable reaction rate. Typically the rhodium concentration lies in the range of from about 20 parts per million up to about 500 parts per million, e.g. in the range of from about 40 to about 300 parts per million, calculated as rhodium metal.

The rhodium may be introduced into the reaction medium in any convenient form. For example, the rhodium salt of an organic acid can be combined with the ligand in the liquid phase and then hydrogenated, prior to introduction of the compounds of formula (IV) and the hydrogen/carbon monoxide mixture. Alternatively the catalyst can be prepared from a carbon monoxide complex of rhodium, such as dirhodium octacarbonyl, by heating with the ligand which thereby replaces one or more of the carbon monoxide molecules. It is also possible to start with the ligand of choice and rhodium metal, or with an oxide of rhodium (e.g. Rh$_2$O$_3$) and the ligand, and to prepare the active species in situ during the course of the hydroformylation reaction. Yet again it is possible to introduce into the reaction medium, as a catalyst precursor, a rhodium complex such as (pentane-2,4-dionato)dicarbonyl rhodium (I) (i.e. the dicarbonyl complex of rhodium formed with acetylacetone), which is then converted under the hydroformylation conditions to the catalytic species which has been postulated to be rhodium hydridocarbonyl tris(triphenylphosphine), i.e. HRh(CO)(PPh$_3$)$_3$. Alternatively the rhodium can be introduced as HRh(CO)(PPh$_3$)$_3$. Other suitable catalyst precursors include rhodium carbonyl triphenylphosphine acetylacetonate, Rh$_4$(CO)$_{12}$ and Rh$_6$(CO)$_{16}$. Further details regarding suitable rhodium-containing hydroformylation catalysts can be obtained, for example, from U.S. Pat. No. 3,527,809.

The reaction can be carried out in the presence or in the absence of an added organic solvent. If a solvent is used it may be, for example, benzene, toluene, isopropanol, diethyl ether, cyclohexanone, or a mixture of aldehyde condensation products such as is disclosed in British patent specification No. 1338237. The compound of formula (IV) can serve as a solvent for the catalyst species and the reaction product(s).

In addition to the rhodium complex catalyst species, the compound of formula (IV) and the product or products of formulae (V) or (VI), the reaction medium may further include excess triorganophosphine ligand. Typically at least about 2 moles up to about 100 moles or more, e.g. up to about 1000 moles or more, of excess free triorganophosphine per gram atom of rhodium may be present in the reaction medium. The upper limit to the amount of free triorganophosphine will be set by its solubility in the reaction medium under the chosen hydroformylation conditions. When using triphenylphosphine, for example the concentration of free triorganophosphine may range up to about 30% by weight or more, e.g. up to about 50% by weight, of the reaction medium.

It will usually be preferred to supply make up carbon monoxide and hydrogen to the reaction medium at an approximately 1:1 molar ratio, e.g. at a ratio of about 1.05:1.

The temperature of the reaction medium may range from a threshold temperature below which the catalyst is effectively inert up to a maximum temperature at which the catalyst is either destroyed or deactivated. Typically the reaction temperature, when using a rhodium complex catalyst, ranges from room temperature upwards, for example from about 30° C. up to about 120° C. or more, e.g. up to about 160° C. It will usually be preferred to operate at a temperature of at least about 60° C., e.g. about 70° C. to about 110° C.

The partial pressure of hydrogen, when using a rhodium complex catalyst, may range from about 0.1 kg/cm$^2$ absolute up to about 20 kg/cm$^2$ absolute. The partial pressure of carbon monoxide may range also from about 0.1 kg/cm$^2$ absolute up to about 10 kg/cm$^2$ absolute or more.

The triorganophosphine ligand may be an aliphatic phosphine, such as tributyl phosphine, but is preferably an aromatic phosphine, such as triphenylphosphine. Other triorganophosphines that can be mentioned include tri-(naphthyl-1)-phosphine, tri-(naphthyl-2)-phosphine, tri-(o-, m- or p-tolyl)-phosphine, tri- (o-, m- or p-methoxyphenyl)-phosphine, and p- N,N-dimethylaminophenyl diphenylphosphine. The preferred tri-organophosphine is triphenylphosphine.

The process of the invention may be carried out discontinuously or batchwise, as for example in a pressurised batch reactor. However, it will usually be preferred to operate the process continuously. Thus the process can be conducted using a liquid recycle process in which reactor solution is passed to a product recovery zone from which catalyst-containing solution is recycled to the hydroformylation reactor. Such a product recovery zone may, for example, comprise a distillation column maintained at a lower pressure than the pressure in the hydroformylation reactor so that the compound or compounds of formula (I) is or are recovered as an overhead vaporous product.

The compound of formula (IV) used as starting material can be prepared in conventional manner by reaction of allyl alcohol with an olefin of formula

(VII)

wherein R$_1$, R$_2$, R$_3$ and R$_4$ have the meanings ascribed to them above, in the presence of an acidic catalyst. As examples of compounds of formula (VII) there can be mentioned iso-butylene, 2-methylbut-1-ene, 2-methylbut-2-ene, 2,3-dimethylbut-2-ene, 3-methylpent-2-ene, 2-ethylbut-1-ene, 1-methyl-cyclohexene, and 1-methyl-cyclopentene. Hence illustrative compounds of formula (IV) include:

allyl t-butyl ether
allyl 2-methylbut-2-yl ether
allyl 2,3-dimethylbut-2-yl ether
allyl 3-methylpent-3-yl ether
allyl 3-ethylhex-3-yl ether
allyl 5-propylnon-5-yl ether
allyl 1-methylcyclohexyl ether
allyl 1-methylcyclopentyl ether Specific examples of compounds of the formula (I) include:

4-t-butoxybutyraldehyde
3-t-butoxy-2-methylpropionaldehyde
4-(2'-methylbutan-2'-oxy)-butyraldehyde
3-(2'-methylbutan-2'-oxy)-2-methylpropionaldehyde
4-(2',3'-dimethylbutan-2'-oxy)-butyraldehyde
3-(2',3'-dimethylbutan-2'-oxy)-2-methylpropionaldehyde
3-(3'-methylpentan-3'-oxy)-2-methylpropionaldehyde
4-(3'-ethylhexan-3'-oxy)-butyraldehyde
3-(3'-ethylhexan-3'-oxy)-2-methylpropionaldehyde
4-(5'-propylnonan-5'-oxy)-butyraldehyde
3-(5'-propylnonan-5'-oxy)-2-methylpropionaldehyde
4-(1'-methylcyclohexanoxy)-butyraldehyde
3-(1'-methylcyclohexanoxy)-2-methylpropionaldehyde
4-(1'-methylcyclopentanoxy)-butyraldehyde
3-(1'-methylcyclopentanoxy)-2-methylpropionaldehyde In the etherification of allyl alcohol the reaction with the olefin is conveniently effected in the presence of an acidic catalyst. The etherification is a reversible reaction and is favoured by the use of low temperatures, for example a temperature in the range of from about 0° C. to about 80° C. Usually it will be preferred to effect etherification of allyl alcohol at about 60° C. or less, preferably in the range of from about 15° C. to about 60° C. for example in the range of from about 35° C. to about 60° C. Since the olefin may be volatile it may be necessary to effect the etherification reaction under elevated pressure. Typical acidic catalysts include ion exchange resins, preferably in anhydrous form, containing sulphonic acid and/or carboxylic acid groups, such as Amberlyst 15 and Dowex 50 resins, as well as aqueous acids, e.g. aqueous solutions of phosphoric acid or dilute aqueous solutions of sulphuric acid (containing, for example, 10% w/v sulphuric acid or less), acid zeolites, acid clays, and organic acids such as p-toluenesulphonic acid or formic acid.

The compounds of formula (I) are useful intermediates for the production of other chemicals. For example, compounds of the formula (V) can be oxidised and then deetherified to form butyrolactone, as described in copending patent application Ser. No. 139,592 filed simultaneously herewith, or can be reduced and then deetherified to form butane-1,4-diol, as described in our copending patent application No. 139,570 filed simultaneously herewith, or can be reduced, deetherified and cyclo-dehydrated to form tetrahydrofuran, as described in our copending patent application No. 139,568 filed simultaneously herewith.

The invention is further illustrated by reference to the following Examples.

EXAMPLE 1

A. Preparation of allyl t-butyl ether 50 ml allyl alcohol and 5 g dry Amberlyst 15 resin were placed in a 300 ml capacity autoclave agitated by means of a Magnedrive unit actuating an induction stirrer. (The word "Amberlyst" is a Registered Trade Mark). The autoclave was purged with iso-butylene and then warmed to 30° C. in an oil bath and pressurised to 1.75 kg/cm² absolute with iso-butylene. The pressure dropped as reaction took place and further iso-butylene was introduced to raise the pressure once again to 1.75 kg/cm². This procedure was repeated as necessary until reaction was complete after approximately 90 minutes as indicated by the cessation of uptake of iso-butylene. After releasing the pressure the product was decanted from the resin and washed several times with deionised water. The crude product was subjected to a partial vacuum to remove iso-butylene (until gas chromatography showed that there was less than 0.1% iso-butylene in the product) and then dried over anhydrous sodium carbonate. Gas chromatography, using a gas chromatograph with a flame ionisation detector and temperature programming, indicated that allyl t-butyl ether had been formed with greater than 98% efficiency. The chromatographic column was 1.83 m × 3.2 mm O.D. stainless steel, packed with 10% by weight diethylene glycol succinate on Chromosorb W.

B. Hydroformylation of allyl t-butyl ether

The same autoclave was charged with the calculated quantities of $HRh(CO)(PPh_3)_3$ and $PPh_3$ and then sufficient Filmer 351 was added to bring the volume of liquid to 90 ml. (Filmer 351 is a complex mixture of polymeric condensation products of n- and iso-butyraldehydes of the type disclosed in British Pat. No. 1338237). The autoclave was then sealed. The body of the autoclave was immersed in an oil bath capable of being heated and thermostatically controlled to ±1° C. between 40° C. and 180° C. by means of a heater/stirrer. The pressure within the reactor could be monitored by means of a pressure transducer linked to a single pen recorder. The stirrer was switched on and its speed adjusted to 500 r.p.m. The reactor was purged with a hydrogen/carbon monoxide gas mixture, the composition of which depended on the planned $H_2:CO$ ratio. The reactor was then pressurised to a level which was 0.35 kg/cm² below the desired operating pressure and isolated. The stirrer speed was then adjusted to 2000 r.p.m. and the temperature increased to the desired value. The pressure was then increased to the required level using the same $H_2/CO$ mixture and the reactor isolated once more. Subsequently 10 ml of allyl t-butyl ether were pumped into the reactor, whereupon reaction commenced. The rate of reaction was monitored by timing the pressure drop between two defined levels ±0.07 kg/cm² around the design pressure. When the pressure reached the lower defined level, the reactor was repressurised to a level 0.14 kg/cm² above the design operating pressure with an approximately 1:1 $H_2:CO$ mixture as demanded by the stoichiometric requirements of the reaction and the procedure repeated until the reaction was complete, at which time the rate of pressure drop was negligible. The oil heater/stirrer was then switched off, the hot oil run out of the bath and replaced with cold oil. The oil stirrer was switched on again and the reactor cooled to 40° C. The reactor stirrer was then switched off and the reactor depressurised and opened to permit the reaction solution to be removed for analysis and/or storage.

Analysis of the reaction solution was effected utilising the gas chromatographic method outlined above in Section A. With the aid of an integrator peak areas were computed and from these results molar selectivities were calculated using response factors determined from pure compounds isolated from the reaction solution by preparative chromatography.

The results are set out in the Table.

TABLE

| Run No. | Temp. °C. | Partial Pressure kg/cm² CO | Partial Pressure kg/cm² H₂ | Rh conc. ppm | TPP conc. wt. % | Reaction Products (yield %) PTBE | Unknown | trans-P(=)TBE | ATBE | cis-P(=)TBE | TBMPA | TBBA |
|---|---|---|---|---|---|---|---|---|---|---|---|---|
| 1 | 70 | 0.53 | 0.53 | 200 | 40 | 0.45* | 0.01 | 3.91 | 2.88 | 1.10 | 11.11 | 80.54 |
| 2 | 50 | 0.53 | 0.53 | 1000 | 10 | 0.73 | 0.41 | 4.87 | — | 0.84 | 17.62 | 75.53 |
| 3 | 100 | 0.53 | 0.53 | 200 | 10 | 1.27 | 0.17 | 29.72 | — | 7.43 | 8.75 | 52.66 |
| 4 | 70 | 3.79 | 3.79 | 50 | 10 | 0.86 | 0.28 | 1.05 | 1.43 | 0.35 | 28.61 | 67.42 |
| 5 | 70 | 0.53 | 0.53 | 300 | 20 | 0.74 | 0.33 | 8.57 | trace | 1.93 | 10.16 | 78.27 |

TABLE-continued

| Run No. | Temp. °C. | Partial Pressure kg/cm² | | Rh conc. ppm | TPP conc. wt. % | Reaction Products (yield %) | | | | | | |
|---|---|---|---|---|---|---|---|---|---|---|---|---|
| | | CO | H₂ | | | PTBE | Unknown | trans-P(=)TBE | ATBE | cis-P(=)TBE | TBMPA | TBBA |
| 6 | 80 | 2.35 | 0.95 | 100 | 20 | 0.59 | 0.19 | 1.71 | 1.32 | 0.68 | 21.87 | 73.64 |

Note:
TPP = triphenylphosphine
PTBE = propyl t-butyl ether
trans-P(=)TBE = trans-propen-1-yl t-butyl ether
ATBE = allyl t-butyl ether
cis-P(=)TBE = cis-propen-1-yl t-butyl ether
TBMPA = 3-t-butoxy-2-methylpropionaldehyde
TBBA = 4-t-butoxy butyraldehyde The reaction residues from these and other experiments were combined and subjected to distillation. 4-t-butoxybutyraldehyde was obtained as a colourless liquid.

EXAMPLE 2

A. Hydroformylation of allyl t-butyl ether 0.10 gms rhodium hydridocarbonyl tris-(triphenylphosphine), i.e. $RhH(CO)(PPh_3)_3$, 90 ml allyl t-butyl ether and 10.0 gms triphenylphosphine were charged to a 300 ml autoclave fitted with a magnetically coupled stirrer, a gas inlet dip tube and an outlet valve. The autoclave was sealed, purged with nitrogen whilst stirring its contents, and isolated. Stirring was continued whilst the temperature of the autoclave was raised to 73° C. by immersion in an oil-bath fitted with a thermostatically-controlled heater-stirrer. The autoclave was then purged with a 1:1 molar $H_2:CO$ mixture and pressurised to 2.1 kg/cm² absolute by closure of the outlet valve. Reaction commenced and proceeded smoothly with a slight exotherm at the beginning of the reaction. As the reaction proceeded, the pressure dropped; when the total pressure reached 1.9 kg/cm² absolute, more 1:1 $H_2:CO$ mixture was admitted to the autoclave to restore the pressure to 2.1 kg/cm² absolute. This repressurisation technique was repeated as necessary until no more gas was taken up, indicating that reaction was complete. This took between 3 and 4 hours. The autoclave was cooled, depressurised and opened, and the contents discharged and stored under nitrogen.

The resulting solution was analysed by gas chromatography using helium as carrier gas, a column packed with 10% w/w diethylene glycol succinate on Chromosorb PAW and a flame ionization detector. Selectivities were observed as follows:

5.6% to isomerised/hydrogenated allylic feedstock
18.9% to 3-t-butoxy-2-methylpropionaldehyde (TBMPA)
75.5% to 4-t-butoxybutyraldehyde (TBBA).

These selectivities are expressed in molar percentages.

The two aldehyde-ethers (TBMPA and TBBA) were separated by distillation from the other constituents of the reaction solution and then purified by distillation and characterised by formation of dimedone derivatives and by measurement of physical data. The following results were obtained.

| Property | TBMPA | TBBA |
|---|---|---|
| Refractive index (at 23° C.) | 1.4128 | 1.4170 |
| Melting point of dimedone derivative | 107–109° C. | 133–135° C. |
| Specific gravity at 25° C. | 0.849 | 0.868 |
| Boiling point | | |
| at 743 mm Hg | 151.6° C. | 169.5° C. |
| at 760 mm Hg | 152.3° C. | 170.5° C. |
| at 100 mm Hg | 103.2° C. | 115.6° C. |

Nuclear magnetic resonance spectra were obtained for the compounds as follows, using tetramethyl silane as an internal standard and carbon tetrachloride as solvent:

| Identifying letter of C-atom to which H-atom is attached | Nature of peak | Chemical shift δ relative to TMS |
|---|---|---|
| 1. TBBA $(CH_3)_3C-O-CH_2-CH_2-CH_2-CHO$ | | |
| a b c d e | | |
| a | singlet | 1.13 |
| b | triplet | 3.31 |
| c | triplet of triplets | 2.39 |
| d | doublet of triplets | 1.84 |
| e | triplet | 9.62 |
| 2. TBMPA $(CH_3)_3C-O-CH_2-CH(CH_3)-CHO$ | | |
| a b c d e | | |
| a | singlet | 1.16 |
| b | doublet | 3.56 |
| c | complex multiplet | 2.39 |
| d | doublet | 1.04 |
| e | doublet | 9.66. |

In each case the ratios of the peak areas corresponded to the expected ratios are predicted from the respective assigned structural formula. In the case of the doublets, triplets and multiplets the quoted chemical shift is the centered value.

EXAMPLE 3

A. Preparation of allyl 2-methylbut-2-yl ether 100 gms 2-methylbut-2-ene, 300 gms allyl alcohol and 10 gms Amberlyst 15 resin were charged to a 1-liter flat-bottomed flask containing a magnetic follower and fitted with a stopper incorporating a gas inlet tube dipping below the surface of the liquid in the flask and with an exit tube leading from the gas space to a Drechsel bottle filled with water. The flask was purged with nitrogen and then placed in a water bath at 30° C. on a magnetic stirrer. The contents of the flask were maintained at this temperature for 16 hours and then filtered. After washing 5 times with deionised water, each time at an approximately 1:1 ratio by volume, in order to remove the bulk of the unreacted allyl alcohol, the resulting organic layer was dried over anhydrous sodium carbonate and the ether was purified by distillation. The yield was 137 gms (74.9% based on the olefin), b.p. 125°–127° C. at 770 mm Hg.

B. Hydroformylation of allyl 2-methylbut-2-yl ether

When 90 ml of allyl 2-methylbut-2-yl ether was used as feedstock, in place of allyl t-butyl ether, in the hydroformylation procedure of Example 2, the following selectivities (expressed in molar percentages) were observed:
7.4% to isomerised/hydrogenated allylic feedstock
19.4% to 3-(2'-methylbutan-2'-oxy)-2-methylpropionaldehyde
73.2% to 4-(2'-methylbutan-2'-oxy)-butyraldehyde.

EXAMPLE 4

A. Preparation of allyl 2,3-dimethylbut-2-yl ether

The procedure of Part A of Example 3 was repeated utilising 100 gms of 2,3-dimethylbut-2-ene in place of the 100 grams of 2-methylbut-2-ene. This resulted in a yield of 88 gms of allyl 2,3-dimethylbut-2-yl ether (52.1% based on the olefin), b.p. 144°–147° C. at 765 mm Hg.

B. Hydroformylation of allyl 2,3-dimethylbut-2-yl ether

The hydroformylation procedure of Example 2 was repeated utilising 90 ml of allyl 2,3-dimethylbut-2-yl ether in place of allyl t-butyl ether. The selectivities achieved (expressed in molar percentages) were as follows:
6.0% to isomerised/hydrogenated allylic feedstock
19.2% to 3-(2',3'-dimethylbut-2'-anoxy)-2-methylpropionaldehyde
74.6% to 4-(2',3'-dimethylbutan-2'-oxy)-butyraldehyde.

EXAMPLE 5

A. Preparation of allyl 1-methylcyclohexyl ether

The procedure of Part A of Example 3 was repeated using 100 gms of 1-methylcyclohexene as the olefin in place of iso-butylene. The yield of allyl 1-methylcyclohexyl ether was 93.5 gms (58.3% based on the olefin), b.p. 138°–140° C. at 240 mm Hg.

B. Hydroformylation of allyl 1-methylcyclohexyl ether

When 90 ml of allyl 1-methylcyclohexyl ether was utilised as feedstock in the hydroformylation procedure of Example 2 the selectivities (expressed in molar percentages) were as follows:
8.0% to isomerised/hydrogenated allylic feedstock
19.0% to 3-(1'-methylcyclohexanoxy)-2-methylpropionaldehyde
73.0% 4-(1'-methylcyclohexanoxy)-butyraldehyde.

We claim:

1. Aldehyde-ethers of the general formula:

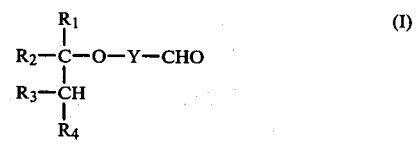

(I)

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, and wherein Y represents —$CH_2$—$CH_2$—$CH_2$— or —$CH_2$—$CH(CH_3)$—.

2. Aldehyde-ethers according to claim 1, in which $R_1$ and $R_2$ each represent, independently of the other, a methyl or ethyl group, $R_3$ represents a hydrogen atom or a methyl group, and $R_4$ represents a hydrogen atom.

3. 4-t-butoxybutyraldehyde.

4. 3-t-butoxy-2-methylpropionaldehyde.

5. An aldehyde-ether of the formula:

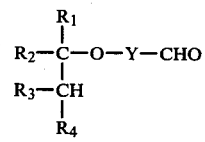

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical and wherein Y represents —$CH_2$—$CH_2$—$CH_2$ or —$CH_2$—$CH(CH_3)$—.

* * * * *